United States Patent
Whynall et al.

(10) Patent No.: US 6,604,405 B2
(45) Date of Patent: Aug. 12, 2003

(54) MONITORING SYSTEM

(75) Inventors: Jeffrey M. Whynall, Killingworth, CT (US); Michael A. Pawlyk, Ansonia, CT (US); Paul Saubestre, Hamden, CT (US); Arnaud Goossens, Portland, CT (US)

(73) Assignee: Bacou USA Safety, Inc., Smithfield, RI (US)

( * ) Notice: Subject to any disclaimer, the term of this patent is extended or adjusted under 35 U.S.C. 154(b) by 144 days.

(21) Appl. No.: 09/774,513

(22) Filed: Jan. 31, 2001

(65) Prior Publication Data

US 2002/0101247 A1 Aug. 1, 2002

(51) Int. Cl.[7] ............... G01N 1/00; G01N 21/35; G01N 33/22
(52) U.S. Cl. ............ 73/23.31; 73/23.2; 73/31.05; 73/863; 422/83; 422/94
(58) Field of Search ............... 73/23.31, 23.2, 73/31.05, 863, 863.01; 422/83, 94

(56) References Cited

U.S. PATENT DOCUMENTS

| | | | |
|---|---|---|---|
| 2,083,520 A | 6/1937 | Miller | 422/83 |
| 2,166,104 A | 7/1939 | Collbohm | |
| 3,560,160 A * | 2/1971 | Lanneau | 73/23.31 |
| 4,013,413 A | 3/1977 | Stewart et al. | |
| 4,134,289 A * | 1/1979 | Bohl et al. | 73/23.31 |
| 4,633,413 A | 12/1986 | Caveney et al. | |
| 4,683,212 A | 7/1987 | Uffenheimer | |
| 5,158,748 A | 10/1992 | Obi et al. | |
| 5,487,312 A | 1/1996 | Kahl et al. | 73/863.01 |
| 5,596,154 A | 1/1997 | Baughman | 73/863.01 |
| 5,918,256 A * | 6/1999 | Delaney | 73/23.31 |

* cited by examiner

*Primary Examiner*—Daniel S. Larkin
(74) *Attorney, Agent, or Firm*—Alix, Yale & Ristas, LLP

(57) ABSTRACT

A system for monitoring gases including sample, dilution, test, and control subsystems. The sample subsystem has a gas probe assembly defining a first end of a sample line and disposed in an area or adjacent to an object to be monitored. A sample pump in the sample line provides a positive motive force for drawing a sample and a sample pressure detector provides a sample pressure signal which is proportional to the sample flow rate. The dilution subsystem includes a dilution line having a first end vented to atmosphere. A dilution pump mounted in the dilution line provides a positive motive force for drawing the dilution air and a dilution pressure detector provides a dilution pressure signal which is proportional to the dilution flow rate. The test subsystem includes a test line having a first end in fluid communication with the second ends of the sample and dilution lines. At least one gas sensor senses the presence of a gas in the test line and provides a gas signal proportional to the level of sensed gas in the test line.

20 Claims, 2 Drawing Sheets

MONITORING SYSTEM

BACKGROUND OF THE INVENTION

This invention relates generally to monitoring systems having a continuously operating gas analyzer. More particularly, the present invention relates to area monitoring systems having "dilution" source for supplying oxygen to a continuously operating combustible gas sensor.

The most common atmospheric danger in industry today is oxygen deficiency. Oxygen may be below the naturally occurring level of 20.9% by volume either due to consumption or displacement. Consumption sources include internal combustion engines and biological consumption sources, such as aerobic organisms. Displacement of oxygen can occur by the introduction of heavier-than-air gases into a confined space. Explosive gas dangers are the second most common hazard. Methane gas can result from the decomposition of organic matter in wastewater treatment plants and landfills. Natural gas leaks (methane) is a perpetual urban problem in sewers and subways. Propane gas can leak out of storage tanks or distribution piping.

Carbon monoxide and hydrogen sulfide are the two most commonly found toxic gases. Hydrogen sulfide is a byproduct of the decomposition of organic matter and can be present in significant concentrations in wastewater treatment plants and landfills. Hydrogen sulfide is also found in mining and oil fields, or wherever water comes in contact with elemental sulfur.

Federal regulations require that employers protect their workers from unsafe breathing atmospheres. The most common places where the atmosphere may not be safe are "confined spaces", for example wells, tanks, vessels, vaults, and unventilated rooms. Where access to such spaces is required and it is undesirable or impossible to spot test the atmosphere of such space prior to each entry, continuously operating area monitoring systems are frequently utilized. Other applications for area monitoring systems where unsafe atmospheres exist include steel mills, warehouses and parking garages (carbon monoxide danger), fertilizer manufacturing (ammonia danger), and plating operations (hydrogen cyanide).

Atmospheric sampling is conventionally accomplished by either a diffusion method or manual/continuous sample-draw. Diffusion allows for sampling the atmosphere only in the immediate area of the detector. Random air currents serve to deliver the detected gas to the sensor face. Sample-draw systems bring the gas sample from a remote location through tubing or pipes to the gas sensor. Manual sample-draw systems use a hand actuated aspirator bulb to pump the sample. Continuous sample-draw systems include the use of a battery-powered or mains-powered motorized sample draw pump.

A common application for industrial safety gas detection is the detection of explosive gases in reaction vessels that contain atmospheres largely comprised of nitrogen. Reaction vessels used for the refinery of petroleum products contain layers of catalyzing beds. These beds must be periodically replaced with new catalyzing material. The old catalyzing material is laden with volatile hydrocarbons that present an explosion risk. To eliminate the risk of explosion while workers are removing the old catalyst, the vessel is filled with nitrogen while the workers wear supplied air respirators or Self-Contained-Breathing-Apparatus. The atmosphere is still monitored for the presence of explosive gases in case the nitrogen purge is lost. Monitoring instrumentation is typically located outside the hazardous location and is monitored by dedicated personnel utilizing continuous sample-draw gas detection equipment.

The most common technology for monitoring for explosive gases are catalytic or "hot bead" gas sensors. The sensors are constructed by coating tiny coils of platinum wire with a ceramic material, and then doping the coils or "beads" with a catalyst. In operation, sufficient current is directed through the sensor such that the surface temperature of the bead exceeds the temperature at which explosive gases will combust in the presence of oxygen and the catalyst. The temperature of the bead is elevated by heat released by the combustion of the explosive gas. The elevated temperature of the bead is reflected by the increased electrical resistance of the coil of platinum wire. Direct-reading instrumentation use this increased resistance to signal the presence of explosive gas. Hot bead sensors typically require about 10% oxygen concentration to operate.

Conventional monitoring systems utilize a "dilution orifice" to combine fresh air with the sample stream to provide ample oxygen for the combustible gas sensor to operate. In practice, a fitting with an orifice open to the atmosphere is placed in the sample-draw tubing near the gas detector. By design, the orifice has a restriction to air flow about equal to the restriction provided by the length of tubing and any filtration that may be in the sampling system. Often times the orifice is adjustable so that the ratio of sample to dilution by fresh air is 1:1, causing the indicated readings to be halved. The operator must mentally multiply readings as indicated by the gas detector by two to arrive at the true sample readings.

The first of three problems with the use of the dilution orifice is that the dilution ratio can change by unknown amounts as the instrument is being used, thus affecting the indicated readings. The dilution ratio will change as the effective restriction of the sample filter changes as the sample filter becomes soiled. Subtle differences between the ambient pressure in the vicinity of the dilution orifice inlet and the ambient pressure in the vicinity of the sample tube inlet will also change the dilution ratio. Significant pressure changes can occur due to process requirements, inerting, and effects of wind.

The second problem with the use of a dilution orifice is that the user must remember whether the dilution orifice is in use and that the actual readings are twice the indicated readings. The user may forget that the dilution orifice is in use, as it may need to be removed from time to time to make straight un-diluted readings.

The third problem with the use of a dilution orifice is that daily calibrations of the gas measuring equipment must be made with the actual length of sample tube and the actual sample filtration system. This can be burdensome since it is often inconvenient to perform calibrations at the worksite and inconvenient to dismantle the sampling system and bring it along with the instrument to an office or laboratory for calibration.

SUMMARY OF THE INVENTION

Briefly stated, the invention in a preferred form is a monitoring system which comprises sample, dilution, and test subsystems. The sample subsystem includes a gas probe assembly defining a first end of a sample line and disposed in an area or adjacent to an object to be monitored. A sample pump mounted in the sample line provides a positive motive force for drawing a sample. A first sample pressure detector senses the pressure in the sample line intermediate the sample pump and the second end and provides a first sample pressure signal which is proportional to the sample flow rate. The dilution subsystem includes a dilution line having a first end vented to atmosphere. A dilution pump mounted in the dilution line provides a positive motive force for drawing the dilution air. A dilution pressure detector senses the pressure in the dilution line intermediate the dilution pump and the second end and provides a dilution pressure signal which is proportional to the dilution flow rate. The test subsystem includes a test line having a first end in fluid communication with the second ends of the sample and dilution lines. At least one gas sensor senses the presence of a gas in the test line and provides a gas signal proportional to the level of sensed gas in the test line.

Preferably, the sample subsystem also includes a second sample pressure detector for sensing the pressure in the sample line intermediate the first end and the sample pump. A particulate and hydrophobic filter mounted in the sample line intermediate the first end of the sample line and the sample pump removes moisture and particulate matter from the sample. A second particulate filter mounted in the sample line intermediate the first particulate filter and the sample pump provides redundant particulate removal capability. A flow orifice mounted in the sample line intermediate the sample pump and the second end of the sample line facilitates control of the sample flow rate.

Preferably, the dilution subsystem also includes a particulate and hydrophobic filter mounted in the dilution line intermediate the first end of the dilution line and the dilution pump. A flow orifice mounted in the dilution line intermediate the dilution pump and the second end of the dilution line facilitates control of the dilution flow rate.

The gas sensors of the test subsystem may include oxygen sensors, hydrocarbon sensors, infra-red absorption carbon dioxide sensors, and electrochemical toxic gas sensors.

A control subsystem of the monitoring system includes a controller having inputs in electrical communication with the sample pressure detectors, the dilution pressure detector, and the gas sensors. A software program stored in memory within the controller computes a dilution flow rate which is proportional to the dilution pressure signal and a sample signal which is proportional to the gas signal adjusted for the dilution flow rate, such that the sample signal is representative of the level of the sensed gas at the gas probe assembly. This sample signal may be transmitted to a local or remote display of the control subsystem.

The controller may also have an output in electrical communication with the start/stop control of the dilution pump and inputs in electrical communication with dilution pump and sample pump run sensors.

It is an object of the invention to provide a new and improved gas monitoring system It is also an object of the invention to provide a monitoring system which provides a warning signal when the oxygen content in the vicinity of the monitoring system controls drops below a predetermined value.

It is further an object of the invention to provide a monitoring system which provides an indication of the level of the monitored gas where the value of the indication is continuously and automatically adjusted to account for the dilution air flow.

Other objects and advantages of the invention will become apparent from the drawings and specification.

BRIEF DESCRIPTION OF THE DRAWINGS

The present invention may be better understood and its numerous objects and advantages will become apparent to those skilled in the art by reference to the accompanying drawings in which.

DETAILED DESCRIPTION OF THE PREFERRED EMBODIMENT

Figure 1:
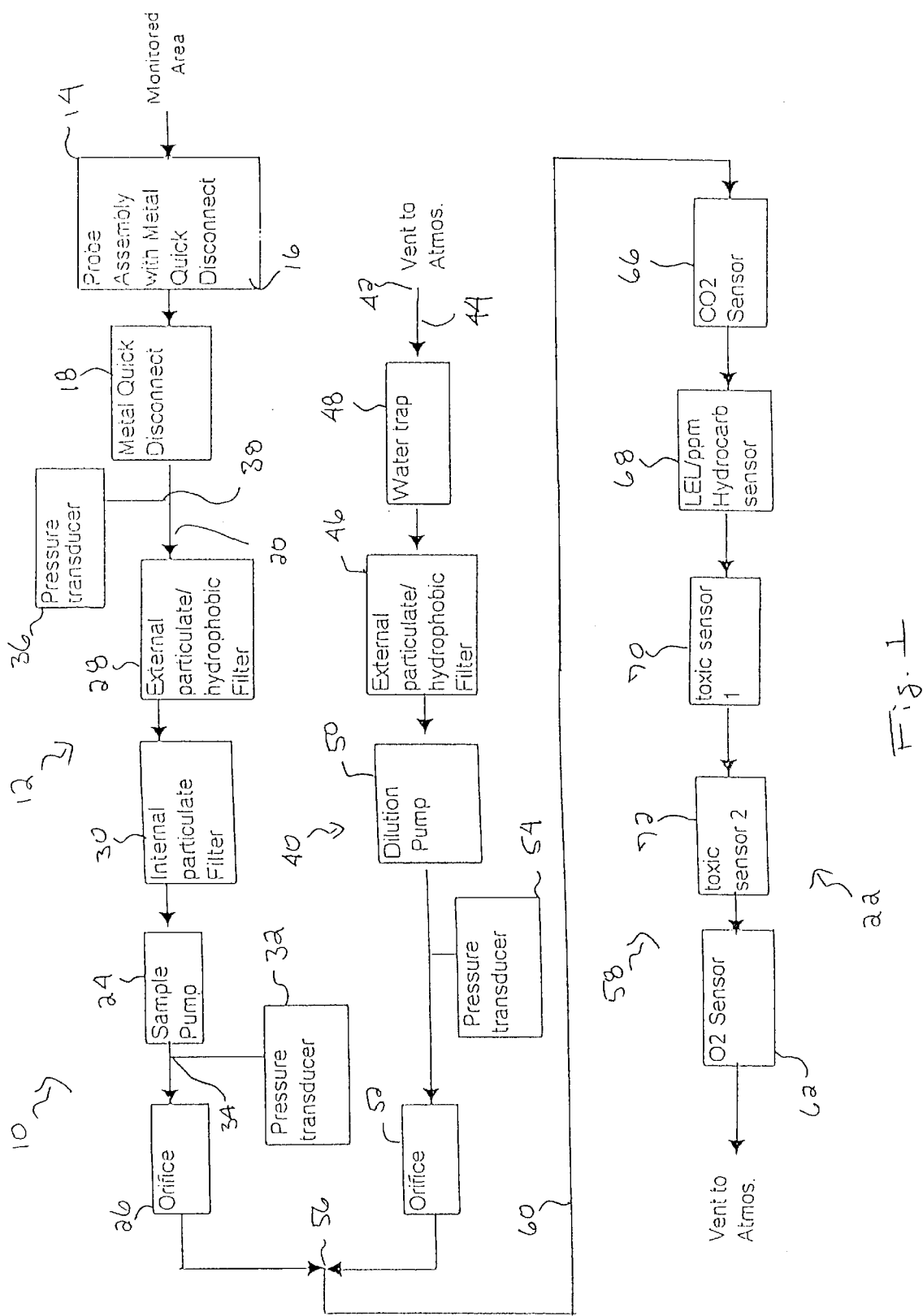
FIG. 1 is a schematic diagram of a monitoring system in accordance with the invention.

With reference to the drawings wherein like numerals represent like parts throughout the several figures, a monitoring system in accordance with the present invention is generally designated by the numeral 10. A monitoring system 10 in accordance with the subject invention includes a sample subsystem 12 and a dilution subsystem which are connected to a test subsystem 58 by a sample line 20 and a dilution line 44, respectively. In its simplest form, the monitoring system 10 is a portable system that is easily transported by an operator for use in short-term area monitoring or for spot detection and measurement. The monitoring system 10 also has particular utility for continuous, long-term monitoring of a specific area.

A monitoring system 10 used to provide continuous, long-term monitoring has a conventional gas probe assembly 14 which is located in the area to be monitored, for example within a reaction vessel. Preferably, a quick disconnect 16 of the probe assembly 14 mates with a corresponding quick disconnect 18 of the monitored area to facilitate installation/removal of the probe assembly 14. Hose extensions with compatible quick disconnects (not shown) of various lengths may be inserted between the probe assembly 14 and the area quick disconnect 18 to provide flexibility of placement for the probe assembly 14. A sample line 20 extending from the area quick disconnect 18 provides a passageway for conducting the sample from the monitored area to the remotely located test equipment 22. A sample pump 24 located in the sample line 20 provides a positive motive force for drawing the sample from the monitored area. An in-line sample orifice 26 downstream of the sample pump 24 provides a means for controlling the flow rate of the sample. Preferably, the sample orifice 26 has a diameter of 0.040 inches.

An external particulate matter and hydrophobic filter 28 in the sample line 20 removes particulate matter and moisture from the atmospheric sample. The filter element of the external filter 28 must periodically be replaced as it becomes loaded with particulate matter. An internal particulate filter 30 is located downstream of the external filter 28. This redundant particulate filtering capacity ensures that the monitoring system 10 is not operated without a sample line particulate filter in the event that the operator removes an exhausted filter element from the external filter 28 and does not replace it with a new filter element or in the event of failure of the external filter 28.

A first sample pressure detector 32 is connected to the sample line 20 via a tap 34 located intermediate the sample pump 24 and the sample orifice 26 provides a means for monitoring the flow rate of the sample through the sample line 20. A second sample pressure detector 36, connected to the sample line 20 via a tap 38 located intermediate the external filter 28 and the area quick disconnect 18, monitors the sample pump generated vacuum at the inlet to the sample line 20.

A dilution subsystem 40 provides oxygen for use by the test apparatus 22 of the monitoring system 10. The upstream end 42 of the dilution line 44 is vented to atmosphere outside of the monitored area, preferably in the vicinity of the test apparatus 22. An external particulate matter and hydrophobic filter 46 in the dilution line 44 removes particulate matter and moisture from the dilution air. A water trap 48 upstream of the external filter 46 provides redundant water removal capability.

A dilution pump 50 located in the dilution line 44 provides a positive motive force for drawing the dilution air. An in-line dilution orifice 52 downstream of the dilution pump 50 provides a means for controlling the flow rate of the dilution air. Preferably, the dilution orifice 52 has a diameter of 0.040 inches. A dilution pressure detector 54 connected to the dilution line 44 intermediate the dilution pump 50 and the dilution orifice 52 provide a means for monitoring the flow rate of the dilution air through the dilution line 44.

A three-way junction 56 downstream of the sample orifice 26 and the dilution orifice 52 joins the sample and dilution lines 20, 44 of the sample and dilution subsystems 12, 40 to a common test subsystem 58. A test line 60 carries the diluted sample to an array of test equipment 22. The specific test equipment 22 installed in the test subsystem 58 may be customized for each specific application. Generally, the diluted sample is vented to atmosphere after all of the required testing.

The test equipment 22 preferably always includes an oxygen sensor 62 to provide a measure of the oxygen present in the diluted sample. As noted above, the upstream end 42 of the dilution line 44 is generally located in the vicinity of the test equipment 22, outside of the monitored area. A diluted and uncorrected measurement of less than 10.45% oxygen (assuming a 1:1 dilution ratio and 20.9% normal atmospheric oxygen concentration) indicates that the dilution flow being drawn from the area in the vicinity of the test equipment 22 contains less than 20.9% oxygen. Since the control system display 64 is also generally located in the vicinity of the test equipment 22, a low oxygen level would present a danger to the user. Therefore, the inclusion of the oxygen sensor 62 provides a means of protecting against spill-over of inerting gas into adjacent safe areas, a common problem.

As shown in FIG. 1, the test equipment 22 may also include an infra-red absorption carbon dioxide sensor 66 for sensing the presence and providing a measure of the quantity of carbon dioxide in the diluted sample. A hydrocarbon sensor 68 senses the presence and provides a measure of the quantity of hydrocarbons in the diluted sample, where such hydrocarbons are indicative of the explosive gas danger. Alternatively, the hydrocarbon sensor 68 may be used for spot detection and measurement. For example, the hydrocarbon sensor 68 may be used to detect the presence of accelerants at the scene of a suspect fire.

One or more electrochemical toxic gas sensors 70, 72 may be utilized to detect the presence and provide a measure of specific toxic gasses. For example, the toxic sensors 70, 72 may include sensors for detecting and measuring the level of solvents or chlorine. The toxic sensors 70, 72 may be of particular utility when the monitoring system 10 is used for spot detection and measurement.

Figure 2:
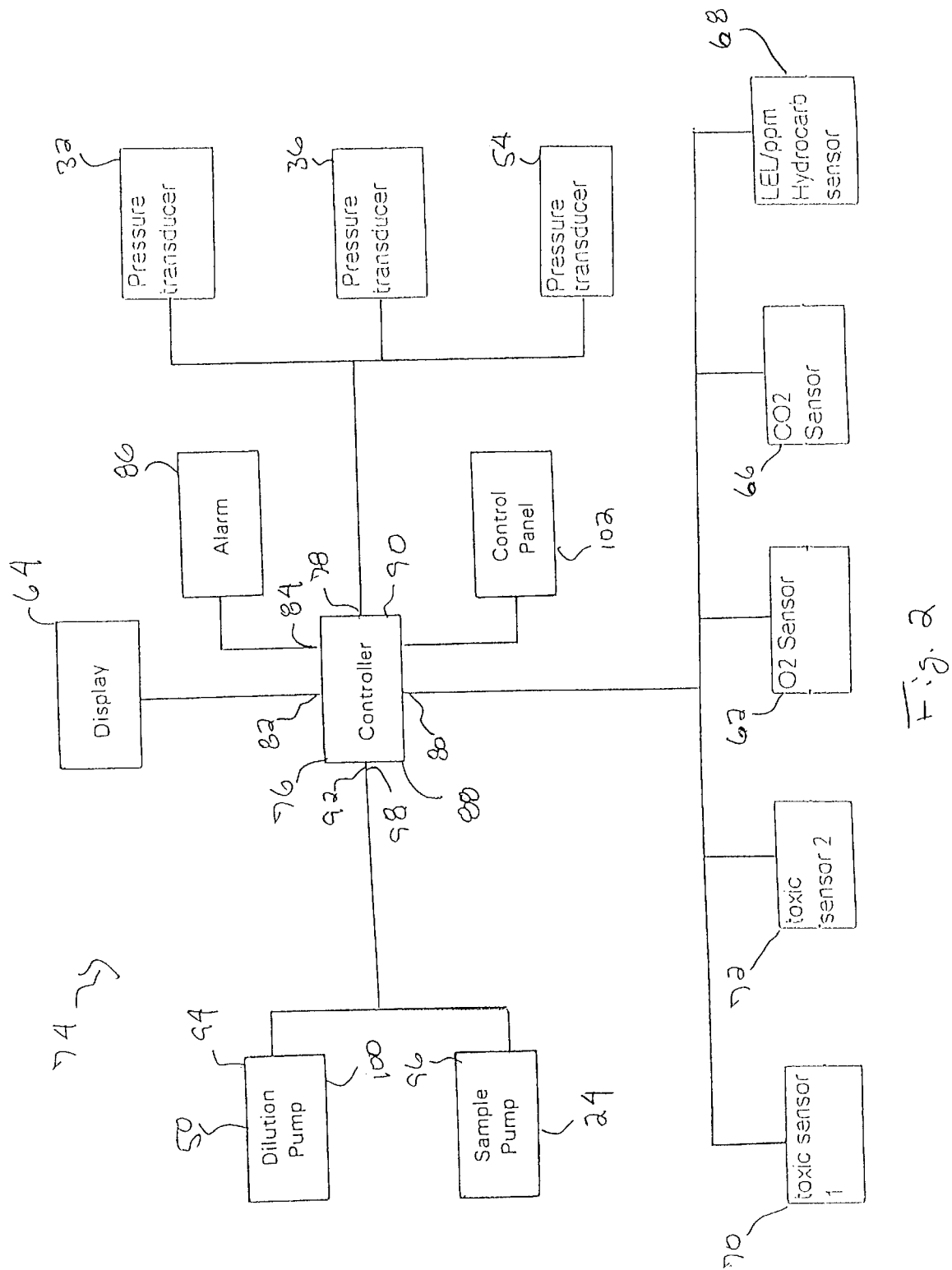
FIG. 2 is a schematic diagram of the control subsystem of the monitoring system of FIG. 1.

With reference to FIG. 2, the control subsystem 74 of the area monitoring system 10 includes a controller 76 having inputs 78, 80 for receiving pressure signals from the first and second sample pressure detectors 32, 36, the dilution pressure detector 54, and the test equipment 22. Preferably, the controller 76 has outputs 82, 84 to a display 64 and/or an alarm 86, located with the controller 76 or at a remote location, for selectively displaying the sensed parameters or providing a warning when one or more of the sensed parameters is outside of an acceptable range. Memory 88 in the controller 76 stores the operating software 90 and alarm set points. The controller 76 may have inputs 92 for receiving pump running signals from pump running detectors 94, 96 on the dilution pump 50 and/or sample pump 24 and an output 98 for controlling the start/stop control 100 of the dilution pump 50. A control panel 102 provides a means of inputting the alarm set points stored in the memory 88 and initiating control of the dilution pump 50.

The software 90 stored in the controller memory 88 includes a conversion module which automatically corrects the value of the diluted reading based on the actual measured dilution ratio.

A portable monitoring system includes all of the system components described above. The quick disconnect 16 of the probe assembly 14 mates with a corresponding quick disconnect of a portable monitor. Hose extensions with compatible quick disconnects of various lengths may be inserted between the probe assembly 14 and the area quick disconnect to provide flexibility of placement for the probe assembly 14. The external particulate matter and hydrophobic filter 28 may be disposed within the probe assembly, or alternatively, within the portable monitor. All of the remaining components of the sample subsystem 12, the dilution subsystem 40 and the test subsystem 58 are located within the portable monitor, with the upstream end 42 of the dilution line 44 being vented to atmosphere immediately adjacent to the portable monitor.

It should be appreciated that including a second, controllable pump 50 for the dilution stream has two advantages. The first advantage is that the test equipment 22 can now switch between normal un-diluted measurements and diluted measurements on-the-fly under software control. Re-calibration of the test subsystem 58 is not required when switching between the two modes since correction factors for the two modes were saved in non-volatile memory during the calibration process. The user need not remember whether a dilution orifice 52 has been installed.

The second advantage of a second pump 50 is that flow changes and thus dilution ratios are much less affected by sample tubing restriction changes or pressure changes. This means that the dilution ratio will be less affected by the presence/absence of sample filters 28, 30 or by different lengths of sample tubing, allowing the calibration to take place at a convenient off-site facility without dismantling the sample-draw filtration and tubing system.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A monitoring system comprising:
   a sample subsystem including a sample line having first and second ends, the first end being disposed in an area or adjacent an object to be monitored, a gas probe assembly in fluid communication with the first end of the sample line, a sample pump mounted in the sample line intermediate the first and second ends, and a first sample pressure detector in fluid communication with the sample line intermediate the sample pump and the second end;
   a dilution subsystem including a dilution line having first and second ends, the first end being vented to atmosphere, a dilution pump mounted in the dilution line intermediate the first and second ends, and a dilution pressure detector in fluid communication with the dilution line intermediate the dilution pump and the second end; and a test subsystem including a test line having first and second ends, the first end being in fluid communication with the second end of the sample line and the second end of the dilution line, and at least one gas sensor in fluid communication with the test line.

2. The monitoring system of claim 1 wherein the sample line has a quick disconnect mounted on the first end and the gas probe assembly has a complementary quick disconnect.

3. The monitoring system of claim 2 wherein the sample subsystem further includes at least one extension hose having oppositely disposed first and second ends, a quick disconnect complementary to the quick disconnect of the gas probe assembly mounted on the first end and a quick disconnect complementary to the quick disconnect of the sample line mounted on the second end.

4. The monitoring system of claim 1 wherein the sample subsystem further includes a flow orifice mounted in the sample line intermediate the sample pump and the second end of the sample line.

5. The monitoring system of claim 1 wherein the dilution subsystem further includes a particulate filter mounted in the dilution line intermediate the first end of the dilution line and the dilution pump.

6. The monitoring system of claim 5 wherein the particulate filter is also a hydrophobic filter.

7. The monitoring system of claim 1 wherein the dilution subsystem further includes a flow orifice mounted in the dilution line intermediate the dilution pump and the second end of the dilution line.

8. The monitoring system of claim 1 wherein said at least one gas sensor is an oxygen sensor.

9. The monitoring system of claim 8 wherein said at least one gas sensor is a hydrocarbon sensor.

10. The monitoring system of claim 9 wherein said at least one gas sensor is an infra-red absorption carbon dioxide sensor.

11. The monitoring system of claim 1 further comprising a control subsystem including a controller having inputs in electrical communication with the first sample pressure detector, the dilution pressure detector, and said at least one gas sensor, the first sample pressure detector and the dilution pressure detector each transmitting a pressure signal proportional to the sensed pressure to the controller, and said at least one gas sensor transmitting a gas signal proportional to the sensed gas to the controller.

12. The monitoring system of claim 11 wherein the dilution pump has an start/stop control and the controller has an output in electrical communication with the start/stop control.

13. The monitoring system of claim 12 wherein the dilution pump and the sample pump each have pump run sensors and the controller has inputs in electrical communication with the pump run sensors.

14. The monitoring system of claim 11 wherein the controller further has a memory storing a software program which computes a dilution flow rate and a sample signal, the dilution flow rate being proportional to the pressure signal of the dilution pressure detector and the sample signal being proportional to the gas signal adjusted for the dilution flow rate, wherein the sample signal is representative of the level of the sensed gas at the gas probe assembly.

15. The monitoring system of claim 14, the control subsystem further including a display in electrical communication with the controller, the controller transmitting the sample signal to the display.

16. A monitoring system comprising:

a sample subsystem including a sample line having first and second ends, the first end being disposed in an area or adjacent an object to be monitored, a gas probe assembly in fluid communication with the first end of the sample line, a sample pump mounted in the sample line intermediate the first and second ends, a first sample pressure detector in fluid communication with the sample line intermediate the sample pump and the second end, a second sample pressure detector in fluid communication with the sample line intermediate the first end and the sample pump;

a dilution subsystem including a dilution line having first and second ends, the first end being vented to atmosphere, a dilution pump mounted in the dilution line intermediate the first and second ends, and a dilution pressure detector in fluid communication with the dilution line intermediate the dilution pump and the second end; and a test subsystem including a test line having first and second ends, the first end being in fluid communication with the second end of the sample line and the second end of the dilution line, and at least one gas sensor in fluid communication with the test line.

17. The monitoring system of claim 16 wherein the sample subsystem further includes a first particulate filter mounted in the sample line intermediate the first end of the sample line and the sample pump.

18. The monitoring system of claim 17 wherein the first particulate filter is also a hydrophobic filter.

19. The monitoring system of claim 17 wherein the sample subsystem further includes a second particulate filter mounted in the sample line intermediate the first particulate filter and the sample pump.

20. A monitoring system comprising:

a sample subsystem including a sample line having first and second ends, the first end being disposed in an area or adjacent an object to be monitored, a gas probe assembly in fluid communication with the first end of the sample line, a sample pump mounted in the sample line intermediate the first and second ends, and a first sample pressure detector in fluid communication with the sample line intermediate the sample pump and the second end;

a dilution subsystem including a dilution line having first and second ends, the first end being vented to atmosphere, a dilution pump mounted in the dilution line intermediate the first and second ends, and a dilution pressure detector in fluid communication with the dilution line intermediate the dilution pump and the second end; and a test subsystem including a test line having first and second ends, the first end being in fluid communication with the second end of the sample line and the second end of the dilution line, and an electrochemical toxic gas sensor in fluid communication with the test line.

* * * * *